United States Patent [19]

Lin et al.

[11] Patent Number: 5,078,988
[45] Date of Patent: Jan. 7, 1992

[54] DENTRIFRICES INCLUDING MODIFIED AMINOALKYL SILICONES

[75] Inventors: Samuel Lin, Paramus; Colleen Parriott, Monroe; John P. Viccaro, Whitestone, both of N.Y.; Todd Domke, Clifton, N.J.

[73] Assignee: Chesebrough-Pond's USA Co., Division of Conopco, Inc., Greenwich, Conn.

[21] Appl. No.: 276,719

[22] Filed: Nov. 28, 1988

[51] Int. Cl.$^5$ .......................... A61K 7/16; A61K 7/22
[52] U.S. Cl. ...................................... 424/49; 424/54; 424/78; 556/424
[58] Field of Search .................... 556/424; 528/28, 38; 424/49

[56] References Cited

U.S. PATENT DOCUMENTS

| | | | |
|---|---|---|---|
| 2,806,814 | 9/1957 | Richter | 167/93 |
| 3,032,577 | 5/1962 | Morehouse | 260/448.2 |
| 3,402,191 | 9/1968 | Morehouse | 260/448.2 |
| 3,507,955 | 4/1970 | Osipow | 424/54 |
| 3,544,498 | 12/1970 | Holdstock et al. | 260/29.2 |
| 3,624,120 | 11/1971 | Yetter | 260/448.2 N |
| 3,852,075 | 12/1974 | Basador | 106/11 |
| 3,860,709 | 1/1975 | Abbott et al. | 424/184 |
| 3,956,480 | 5/1976 | Dichter et al. | 424/54 |
| 4,071,614 | 1/1978 | Grimm | 424/49 |
| 4,161,518 | 7/1979 | Wen et al. | 424/52 |
| 4,213,961 | 7/1980 | Curtis et al. | 424/54 |
| 4,243,658 | 1/1981 | Chang | 424/52 |
| 4,246,029 | 1/1981 | Sanders et al. | 106/3 |
| 4,256,731 | 3/1981 | Curtis et al. | 424/54 |
| 4,304,766 | 12/1981 | Chang | 424/52 |
| 4,430,235 | 2/1984 | Chu et al. | 252/49.6 |
| 4,450,152 | 5/1984 | Ona et al. | 424/70 |
| 4,454,110 | 6/1984 | Zeslafsk et al. | 424/54 |
| 4,485,090 | 11/1984 | Chang | 424/52 |
| 4,507,455 | 3/1985 | Tangney et al. | 528/26 |
| 4,510,127 | 4/1985 | Chang | 424/52 |
| 4,994,593 | 2/1991 | Lin et al. | 556/424 |

FOREIGN PATENT DOCUMENTS

| | | |
|---|---|---|
| 689679 | 4/1953 | United Kingdom . |
| 1194885 | 6/1970 | United Kingdom . |
| 1447254 | 8/1976 | United Kingdom . |

*Primary Examiner*—Thurman K. Page
*Assistant Examiner*—James M. Spear
*Attorney, Agent, or Firm*—Gerard J. McGowan, Jr.

[57] ABSTRACT

Dentifrices including modified amino alkyl silicones are provided. The aminoalkyl silicones are modified with epoxides to alkylate the nitrogen atoms and decrease their reactivity to flavors and other aldehydes present in the dentifrice. The modified silicones form a hydrophobic layer on the teeth for prevention of caries and stain.

41 Claims, No Drawings

DENTRIFRICES INCLUDING MODIFIED AMINOALKYL SILICONES

FIELD OF THE INVENTION

The application concerns dentifrices including modified aminoalkylsilicone compounds.

BACKGROUND OF THE INVENTION

Despite the many advances in dentifrice formulation in recent years, there is still a need for improved products. Since the development of anticaries agents, especially the fluorides, has led to a decline in the incidence of tooth caries, attention in the oral health care field has increasingly focused on the problems of gum disease, periodontitis. While antibacterial agents have been proposed for inclusion in products for use by consumers in the treatment of periodontitis, certain problems have been associated with their use. For example, use of chlorhexidine, which has been known as an antibacterial agent, has been associated with staining problems. It produces yellow to dark brown stains on teeth, tongue and oral mucosa. Furthermore, chlorhexidine has a very bitter taste. Cationic antibacterial agents other than chlorhexidine, such as hexetidine, alexidine, and other quaternary ammonium compounds, also cause staining.

There has been a need, therefore, for developing a dentifrice formulation including chlorhexidine or other antibacterial agents, which does not cause staining of the teeth and which has an improved taste. Moreover, dentifrices having improved anticavity effects are still desired.

Staining can be troublesome, whether or not chlorhexidine is the cause. The accumulation of stains on tooth surfaces poses an esthetic problem for many individuals. Staining is promoted by dietary substances such as coffee, tea and red wines, and by smoking.

Plaque is a common factor in caries, gum disease and staining and greatly contributes to their development. Proper oral hygiene as currently practiced requires that plaque be removed or prevented not only for cosmetic purposes but also to eliminate a source of potential injury to teeth and gums.

Plaque is initiated when cariogenic bacteria adhere to pellicle, a proteinaceous film on the surface of teeth. These adherent bacteria metabolize dietary constituents, reproduce and accumulate to form the tenacious deposit known as plaque. Plaque generally consists of bacteria, bacterial end products such as polysaccharides, inorganic salts and salivary proteins. Plaque bacteria ferment dietary carbohydrates to organic acids which demineralize enamel, resulting in tooth decay.

Plaque acts as a nucleus for the formation of calculus (tartar) which is essentially plaque that has been mineralized with calcium phosphate salts. As calculus matures and hardens, it tends to stain noticeably due to adsorption of dietary chromagens. In addition to their unattractive appearance, calculus deposits, at the gum line, are a contributing source of gingivitis and periodontal disease.

Silicones have previously been suggested for inclusion in dentifrice compositions in that it has been proposed that they would coat the teeth and thereby prevent cavities and staining. For example, British Patent Specification 689,679 discloses a mouthwash containing an organopolysiloxane for the purpose of preventing adhesion of, or for removal of, tars, stains, tartar and food particles from the teeth. However, polymers such as those disclosed in the '679 specification have not generally been successfully used for coating the teeth since it has been found that the polysiloxane does not adhere to the teeth for prolonged periods of time. Therefore, the need for dentifrice formulations including a hydrophobic substance which effectively coats the teeth has not been satisfied.

Yetter U.S. Pat. No. 3,624,120 discloses quaternary ammonium salts of cyclic siloxane polymers, which are said to be useful as cationic surfactants, as bactericides and as anticariogenic agents. Yetter indicates that it is believed that the siloxane polymer absorbs onto calcium phosphate to form a film which decreases the rate of acid solubilization. However, due to the solubility of the cyclic, low molecular weight, high N/Si ratio compounds of Yetter, it would not be expected that they could impart a strongly hydrophobic film to the surface of teeth. Moreover, there does not appear to be any disclosure in Yetter that its low molecular weight compounds would have any usefulness in preventing staining. Other problems with the Yetter compounds are their high cost due to the high N/Si ratio. Also, the freedom from toxicity of high N/Si ratio compounds may be questioned.

Viccaro, et al. copending application Ser. No. 07/276,704 filed simultaneously herewith and entitled "Dentifrice Containing Aminoalkyl Silicones" discloses dentifrice formulations including aminoalkylsilicones for coating the teeth and inhibiting stain and caries. The aminoalkylsilicones have been found to be more substantive than alkylsilicones, apparently due to the interaction of the positively charged nitrogen of the amine with the negative charges on the surfaces of the teeth. However, amine groups tend to react with certain chemical groups found in dentifrice components such as the aldehydes of flavoring ingredients. Consequently, aminoalkylsilicones bearing amine groups capable of being protonated over a broad pH yet of reduced reactivity are desirable.

Attempts have been made to modify the structure of aminosilicones to decrease the reactivity of the amino groups. In U.S. Pat. No. 4,507,455 aminosilicones are reacted with acetic anhydride to form amides. It is believed that this modification seriously limits the pH range over which the amines will be protonated, thereby detracting from the usefulness of the respective aminoalkylsilicones in applications, such as those mentioned above, wherein protonation of the amine is significant. Also, U.S. Pat. No. 4,472,566 discloses the reaction of aminosilicones with benzylchloride to yield secondary and tertiary amines.

Morehouse U.S. Pat. No. 3,032,577 discloses organosiloxanes which are said to be useful for a variety of applications in the synthetic polymer art, particularly as flocculating agents for aqueous dispersion of clay. The organosiloxanes of the Morehouse patent include units of the formula:

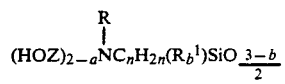

wherein —OZ— is the divalent group derived from a monoepoxide by opening of the oxirane ring, HO is interconnected to N through 2 carbon atoms, a is an integer from 0 to 1, n is an integer from 3 to 15, R may be hydrogen, monovalent hydrocarbon or

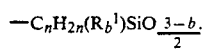

Morehouse does not appear to indicate that his compounds would be useful in dentifrices and the like, nor does he seem to recognize the desirability of using compounds which can yield a higher positive charge density.

SUMMARY OF THE INVENTION

Applicants have discovered that dentifrices which include the compounds selected from the novel class of aminoalkyl silicones of the formulas A and B and from the class of compounds of formulas C and D below form a hydrophobic barrier on the surface of teeth for preventing staining of teeth and in preventing caries. Moreover, the aminoalkylsilicones utilized in the invention have been modified to decrease the reactivity of the amine groups toward aldehydes and other reactive species, yet to retain positive charges over a broad pH range. The antistaining properties of the dentifrices of the invention are of particular significance when the compounds of the invention are used in conjunction with an antimicrobial compound such as chlorhexidine. In such event, the aminoalkyl silicone is used to decrease stain and caries while the antimicrobial compound is employed to decrease bacterial and gum disease without the usual disadvantage of staining and without reaction with flavor components such as aldehydes. The antistaining properties of the modified amino alkyl silicones of the invention may likewise be of use when other staining compounds such as stannous fluoride are included in the dentifrices. In a preferred embodiment, the aminoalkyl silicones which are modified comprise amodimethicones.

The modified silicones of the invention are produced by treating silicones containing primary or secondary amine functional groups with epoxides such as ethylene oxide. This reaction effectively converts most amines to tertiary amines with one or two beta-hydroxylhydrocarbyl substituents. Reaction of primary amines generally yields a tertiary amine with 2 betahydroxylhydrocarbyl substituents. The tertiary molecular structure and the electron withdrawing property of beta-hydroxyls reduce the amine reactivity, but still maintain the pka between seven and nine. Thus, in most formulation conditions, these novel silicones remain as cationic polymers and have good physical interactions with the substrate surface but reduced chemical reactivities toward flavoring agents, dyes and skin.

In the preferred embodiment, the novel modified silicones included in the dentifrices of the invention comprise an organosiloxane including at least one unit of formula A:

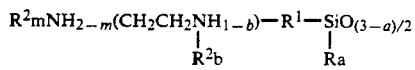

wherein
a is from 0 to 2, n is from 1 to 5, R is a monovalent radical, $R^1$ is a divalent hydrocarbon radical, $R^2$ is

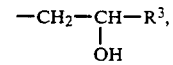

$R^3$ is selected from the group consisting of hydrogen and monovalent hydrocarbon radicals, and m is 1 or 2, b is 0 or 1.

R is preferably selected from the group consisting o hydrocarbon radicals, halogenated hydrocarbon radicals, hydrogen, hydroxyl, and alkoxyl groups. Especially preferred are methyl, phenyl and -trifluoropropyl. Groups of 1 to 10 and more particularly, 1 to 4 carbon atoms are preferred. The divalent hydrocarbon radical of $R^1$ preferably includes from 1 to 20 carbons and even more preferably includes 3 to 20 carbon atoms. Most preferred are hydrocarbon radicals of from 3 to 5 carbon atoms. Preferred $R^3$ groups include hydrogen, hydrocarbon radicals, methyl or phenyl. Where $R^3$ is a hydrocarbon radical, it is preferred that the radical including 10 or fewer carbon atoms, even more preferably 4 or fewer. Hydrogen and methyl are particularly preferred. n is preferably 1; m is preferably 2; and b is preferably 1.

An example of the units of formula A is:

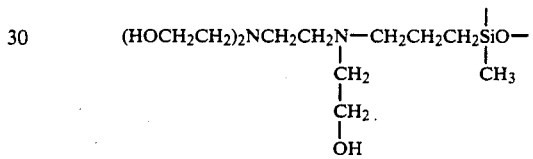

Preferably, the units of Formula A are present in the aminoalkyl silicone with units of Formula B:

wherein $R^4$ and $R^5$ are the same or different monovalent radicals, a and c are integers of 0, 1, 2 or 3 and a plus c is 0, 1, 2 or 3. Preferably $R^4$ and $R^5$ are hydrocarbon radicals, halogenated hydrocarbons, hydrogen, hydroxyl or alkoxyl. Generally, $R^4$ and $R^5$ will include from 1 to 20 carbon atoms, preferably from 1 to 10 carbon atoms, more preferably from 1 to 4 carbon atoms. Methyl, phenyl and -trifluoropropyl are especially preferred for $R^4$ and $R^5$. It is particularly preferred that a plus c equal 2.

The modified aminosilicones of the preferred embodiment of the invention include at least 1 unit of Formula A, and preferably units of Formula B, as well, in the form of a random copolymer, block copolymers, linear polymer or branched polymer. The content of Formula A in the polymer ranges by weight between 0.5% and 100%, preferably between 1% and 10%. The molecular weight of the polymer preferably ranges from 5000 to 100,000. Molecular weights above 5000 are strongly preferred so that the compound will effectively provide a hydrophobic barrier for the surface of the teeth. 100,000 is the preferred molecular weight ceiling. A viscosity in the range of 50 cps to 3000 cps is preferred.

Examples of the modified polysiloxanes of the preferred embodiment of the invention are as follows:

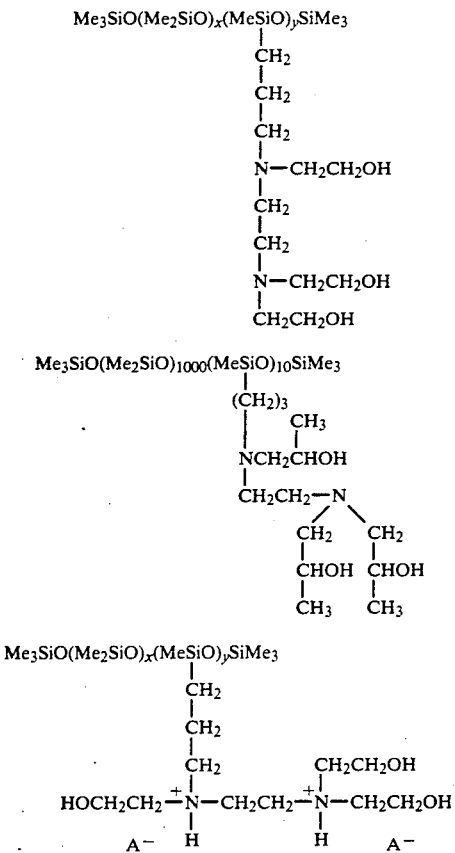

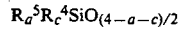

wherein x=1000, y=50 and A⁻ is a counter ion.

Although the embodiment(s) of Formulas A and B is preferred in that it is believed that maximization of positive charge density resulting from use of multiple nitrogens per side chain results in better deposition of the aminoalkylsilicone onto the teeth, dentifrices including an aminoalkyl silicone of Formulas C and D may also be used to advantage. Consequently, the invention also encompasses a dentifrice comprising an organosiloxane copolymer including:

a) at least one unit of $$R_m^2N-R^1-\underset{\underset{R_a}{|}}{SiO_{(3-a)/2}} \qquad C$$

wherein

R, R¹, R², a and m have the meanings of formulas A & B given above; and b) at least one unit of $$R_a^5R_c^4SiO_{(4-a-c)/2} \qquad D$$

wherein

R⁴, R⁵, a and c have the meanings given above.

The modified aminoalkylsilicones of the second embodiment of the invention include at least 1 unit of Formula C and 1 unit of Formula D in the form of a random copolymer, block copolymer, linear polymer or branched polymer. The content of Formula C in the polymer ranges by weight between 0.5% and 100%, preferably between 1% and 10%. The molecular weight of the polymer preferably ranges from 5000 to 100,000. Molecular weights above 5000 are strongly preferred so that the compound will effectively provide a hydrophobic barrier for the surface of the teeth. 100,000 is the preferred molecular weight ceiling. A viscosity of 50 cps to 3000 cps is preferred.

An example of the modified aminoalkylsilicones of the second embodiment of the invention are compounds having at least one unit of the following:

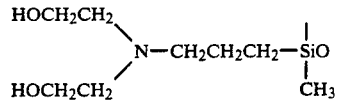

DETAILED DESCRIPTION OF THE INVENTION

The compounds of the invention may be prepared by mixing epoxide compounds with aminosilicones in a pressure reactor and heating for about 24 hours, after which the unreacted epoxide compound is vacuum stripped off. The amount of epoxide to be used is calculated based upon the number of amine functional groups on the aminoalkyl silicone. Preferably, 2 epoxides are reacted for every primary amine and one epoxide for every secondary amine, in order to convert them to tertiary amines. A stoichiometric amount or up to 25% excess of epoxide can be used. The reaction is preferably conducted between 25° C. and 150° C., especially between 50° C. and 100° C. The pressure is preferably maintained from 50 psi to 300 psi, particularly from 50 psi to 150 psi.

Although applicants do not wish to be limited to any particular theory of operation of their invention, it is believed that when the modified aminoalkyl silicones come in contact with water of an appropriate pH, the pendant or endcapping nitrogens are protonated and the cations so formed are attracted to the negatively charged phosphate ions on the teeth. Therefore, the hydrophilic charged pendant or endcapping moieties of the aminoalkyl silicones are attracted to the teeth and form an anchor for the hydrophobic alkyl silicone backbone which forms a film on the teeth and protects them from stains and caries. The B-hydroxylhydrocarbyl groups bonded to the amine-nitrogen decreases the propensity of the nitrogen to react with aldehydes and other reactive groups found in dentifrices while at the same time permitting the nitrogens to become protonated below approximately pH 9.5.

Increasing the number of aminoalkyl groups per molecule enhances the substantivity of the silicone. The increased substantivity of aminoalkyl-containing silicones enables them to impart a durable water repellent barrier to enamel which is compatible with cationic antimicrobial/antiplaque agents. Aminoalkyl silicones do not adversely affect the antiplaque activity of chlorhexidine. On the other hand, while increasing the number of aminoalkyl groups per molecule should improve the association of the molecule with the surface of the tooth, it also tends to increase the solubility and reduce the hydrophobicity of the polymer. Consequently, for all of the embodiments of the invention, it is preferred that the aminoalkyl groups constitute from 1 to 60%, preferably 5 to 30% by repeat unit of the polymer. In other words, it is preferred that the number of silicon atoms which have nitrogen-containing moieties appended thereto constitute from 5 to 30% of the total number of silicon atoms.

The dentifrice of the invention can take several forms. It may, for instance, be a toothpaste, cream or gel, or it may comprise a mouthwash or it may be an oral spray or chewing gum. In its preferred embodiment, the modified aminofunctional silicone of the invention (whether amodimethicones or other amino alkyl silicones,) is present in the form of an emulsion. In a particularly preferred embodiment of the invention, an antimicrobial compound such as chlorhexidine or a quaternary ammonium salt is included in the dentifrice together with the modified aminofunctional silicone. Typical dentifrice ingredients may be included, depending, of course, on the form of the dentifrice. Toothpaste creams and gels will generally include one or more abrasives and may include humectants, binder, surfactant, alcohol, flavoring agents, sweetening agent and water. Mouthwashes will generally include alcohol, humectant, surfactant, flavoring agent, sweetening agent and water. The dentifrice may also take the form of a denture cleaner.

While the primary importance of the invention in the area of gum disease is believed to be the ability to use chlorhexidine, quaternary ammonium compounds and other antimicrobial compounds in a dentifrice without staining the teeth, it is also believed that the compositions of the invention may be useful in prevention of gum disease by reducing or preventing plaque. Indeed, as indicated above, plaque is a common factor in caries, gum disease and staining and greatly contributes to the development of each of these problems.

While it is expected that the film of the alkylamino silicones of the invention will prevent the adhesion of staining materials such as chlorhexidine, it is also believed that removal of such staining materials from the teeth will be facilitated thereby. Insofar as the dentifrices of the invention can reduce staining they would also provide a cosmetic as well as a health benefit. It is also contemplated that the compositions of the invention will reduce pain and progression of root caries via the coating action, will reduce unpleasant tastes from dental product components such as antimicrobials, surfactants, etc. and may prevent calculus growths.

A preferred class of aminoalkyl silicone are the amodimethicones.

The aminoalkyl silicones of the invention are preferably non-cyclic. It is important that the silicones not be cyclized in order to permit them to deposit well onto the teeth. There is no theoretical ceiling on the molecular weights of the silicones so long as they spread onto tooth enamel by brushing action or rinsing. Compounds with molecular weight from 10,000 to 30,000 would be expected to yield more substantive films than compounds having lower molecular weights. High molecular weight silicones form more stable films on the enamel surface whereas silicones of lower molecular weights tend to spread faster. Silicones of high and low molecular weights may be mixed together to obtain mixtures of the desired viscosity.

The dentifrices of the invention preferably comprise a mixture including from 0.5% to 20% by weight, even more preferably from 1% to 5% by weight of the modified organosiloxane polymer. The dentifrice may also include from 0.001% to 3% and more preferably from 0.1 to 1% by weight of an antimicrobial compound, other than the modified aminoalkylsilicone, such as an antimicrobial quaternary ammonium compound or chlorhexidine. The preferred antimicrobial compound is chlorhexidine. The modified aminoalkylsilicone of the invention may be used in a dentifrice according to the invention with or without the antimicrobial compound.

The modified aminoalkyl silicones of the invention may be incorporated into dentifrices as silicone oils or as silicone emulsions, preferably as emulsions. Nonionic surfactants and/or cationic surfactants are preferred emulsifiers. Certain cationic quaternary ammonium surfactants such as tallow trimethylammonium chloride and cetyl pyridinium chloride may be used to advantage in that they also deliver anti-plaque health benefits (antimicrobials) in addition to being emulsifiers.

The amines of the invention become protonated and bear positive charges when the pH is below their pKas. Depending on structure, the pKas will range from about 7 to about 9.5. The pH of the dentifrices of the invention should be below 9.5 and are preferably between 6 and 8 so that the aminoalkyl groups are protonated and degradation of the siloxane polymer is prevented.

The preferred dentifrices are toothpaste creams and gels and mouthwashes. Ingredients which may be included in toothpastes and gels generally and which may be used in toothpaste and gel compositions in accordance with the invention are abrasive polishing materials, sudsing agents, flavoring agents, humectants, binders, sweetening agents, and water. Antitartar agents may be added to enhance the anticalculus affect of the present compositions.

Abrasives which may be used in the dentifrice of the invention include alumina and hydrates thereof, such as alpha alumina trihydrate, magnesium trisilicate, magnesium carbonate, aluminosilicates, such as calcined aluminum silicate and aluminum silicate, calcium carbonate, zirconium silicate, polymethylmethacrylate, powdered polyethylene, silica and the like. Depending on the form which the dentifrice is to take, the abrasive may be present in an amount of from 0 to 70% by weight, preferably 1 to 70% by weight, more preferably from 10 to 70% by weight, particularly for toothpastes.

Humectants contemplated for use in the present invention include glycerol, polyol, sorbitol, polyethylene glycols and propylene glycol. The humectants are generally present in amounts of from 0 to 80%, preferably 5 to 70%, by weight, particularly for toothpastes. Thickeners suitable for use in the invention include silica. Thickeners may be present in toothpaste creams and gels at 0.1 to 20% by weight.

Binders suitable for use in the dentifrice of the invention include hydroxyethyl cellulose (Natrasol) and hydroxypropyl cellulose (Klucel). It is preferred that anionic binders be avoided as it is believed that they complex with the ammonium cations of the protonated aminoalkyl silicone. Binders may be present in the toothpaste of the invention to the extent of from 0.01 to 3%. Sweeteners suitable for use in the present dentifrice, preferably at levels of about 0.1% to 5%, include saccharin.

Certain pyrophosphate and other polyphosphate salts have been disclosed in U.S. Pat. Nos. 4,515,772 and 4,627,977 as being useful as antitartar agents. These include di- and tetraalkali metal pyrophosphates wherein the alkali metals are preferably selected from the group consisting of sodium and potassium. Although phosphates are generally not favored as they tend to react with aminoalkyl silicones, inclusion of these antitartar agents may be appropriate in certain formulations in accordance with our invention. Zinc salts are disclosed as anticalculus agents in U.S. Pat. No. 4,100,269 and in U.S. Pat. Nos. 4,416,867, 4,425,325 and 4,339,432 (with glycine). These may be included in the present compositions.

Surfactants may be included as sudsing agents. As discussed earlier in connection with emulsifying the silicone, it is preferred that surfactants used in a dentifrice according to the invention be nonionic or cationic, although sarcosinate surfactants may be useful. Surfactants may be present within the range of 0 to 15%, preferably 0.1 to 15%, more preferably 0.25 to 10% by weight.

Flavors are usually included in toothpastes in low amounts, such as from 0.01 to about 5% by weight, especially from 0.1% to 5%. Any type of flavor, even flavors with aldehyde groups, may be used. Low- and non-aldehydic flavors would normally be preferred since the amines of the modified silicones would ordinarily be expected to react with the acyl groups of aldehyde to form Schiff bases, which are colored and which would make the nitrogen atoms on the silicones unavailable for interaction with the surface of the tooth. However, the aminoalkylsilicones of the invention are modified to decrease the reactivity of the amine nitrogen. Consequently, the level of aldehydic and other amine-reactive moieties is of less concern.

Fluoride sources used in toothpastes such as sodium fluoride, stannous fluoride, sodium monofluorophosphate, zinc ammonium fluoride, tin ammonium fluoride, calcium fluoride and cobalt ammonium fluoride may be included. Fluoride ions are typically provided at a level of from 0 to 1500 ppm, preferably 50 to 1500 ppm, although higher levels up to, say, 3000 ppm may be used. Casein and its hydrolysate are other potential anticaries agents, e.g., at a level of 0.1 to 5% by weight.

Titanium dioxide is a suitable whitener.

Ingredients mentioned above as suitable for toothpastes are generally suitable for gels, as will be apparent to one of skill in the art of toothpaste and gel formulation. Thus, except where otherwise noted, references to toothpastes are to be construed as applying to gels as well.

Typically, mouthwashes comprise a water/alcohol solution, flavor, humectant, sweetener, sudsing agent, and colorant. The corresponding compounds mentioned above which are used in toothpastes, are generally suitable within the ranges above for mouthwashes as well. The mouthwash can include ethanol at a level of from 0 to 60%, preferably from 5 to 30% by weight.

Where chlorhexidine or other antimicrobial agents such as quaternary ammonium antimicrobial compounds are included in the dentifrice of the invention, their preferred concentration may range from 0.001% to about 4%. Especially preferred concentrations for chlorhexidine range from 0.1% to 1%. Cetylpyridinium chloride, hexetidine, alexidine, phenolics such as DP300 exCiba Geigy and salicylamides (including salicylanilides), and sources of certain metal ions such as zinc, copper, silver and stannous (e.g., zinc, copper and stannous chloride, and silver nitrate) may also be appropriate antibacterial agents. Coburn et al., U.S. Pat. Nos. 4,358,443 and 4,287,191 describe the use of salicylamides and are incorporated by reference herein.

Dyes/colorants suitable for dentifrices, i.e., FD&C Blue #1, FD&C Yellow #10, FD&C Red #40, etc., may be employed in the dentifrices of the invention.

The aminoalkyl polysiloxanes of the invention may be end capped. If end capped, one or more of the end capping groups, Re, preferably includes one or more ethoxylated nitrogen atoms.

As indicated above, a preferred class of aminoalkyl silicones (which are reacted with an epoxide to yield the modified compounds employed in the dentifrice of the invention) is that of the amodimethicones. Amodimethicones are polydimethyl siloxane polymers containing aminoalkyl groups. The aminoalkyl groups may be, for example, n-propylamine or n-propyl-N-ethylenediamine and these may be present either pendent or at one or more ends of the polydimethylsiloxane chain. Amodimethicones are commercially available. Examples of commercially available amodimethicones include Dow Corning's DC-929, DC-Q2-7224 and Q2-8075. These polymers comprise aminoalkyl groups affixed to a predominently polydimethyl siloxane structure. The typical structure of Q2-8075's aminoalkyl group-containing units is:

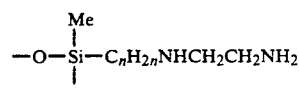

As indicated above, ethoxylated and propoxylated aminosilicone compounds including multiple nitrogen groups per silicon atom (Formula A above) such as compounds including units of the following:

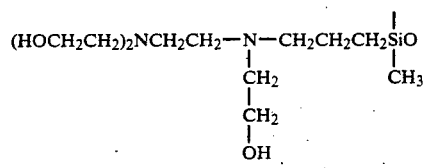

are particularly preferred because they have a higher positive charge density upon protonation. These compounds are described more fully in Lin et al. U.S. patent application entitled "Hydroxylhydrocarbyl-modified Aminoalkyl Silicones" filed simultaneously herewith and incorporated by reference herein.

Unless otherwise specified or required by the context, percentages of ingredients are by weight.

The following specific examples further illustrate the invention, but the invention is not limited thereto.

Alkylation of Amine Functional Silane Monomer

EXAMPLE 1

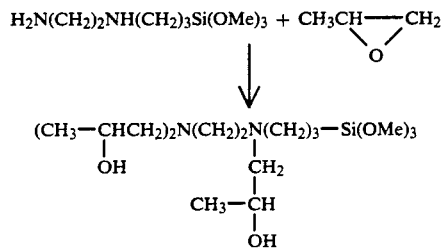

50 g of N-2-amino ethyl-3-amino propyl trimethoxy silane (ex Petrarch), 39.2 g of propylene oxide (ex Aldrich) and 90 g of 2-propanol were reacted together and then stripped off the solvent.

The product was a reactive silicone which precipitated out during the amine titration.

Alkylation of Amino Functional Polydimethyl Siloxane Copolymer

EXAMPLE 2

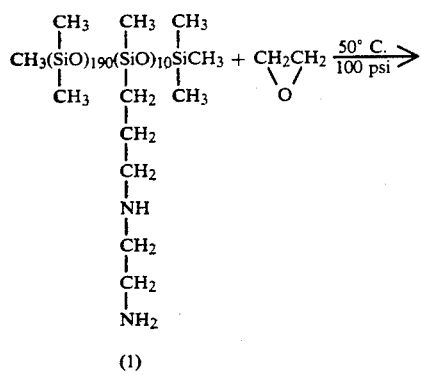

(1)

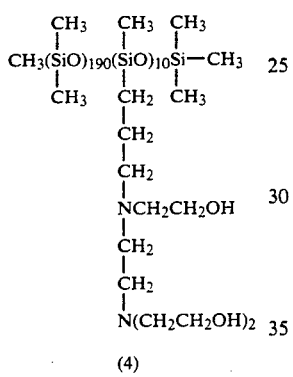

(4)

Into the cooled Parr Pressure Reactor was placed 80 g of amodimethicone Oil (1) and 6.5.g of ethylene oxide. The contents were then heated at 50° C. and 100 psi and stirred for approximately 24 hours. Within 0.5 hours of the start of the reaction, an exotherm was observed at 75° C. After the 24 hour reaction time, the heat was removed and the contents cooled to room temperature. Following this the pressure was released from the reactor and the unreacted epoxide removed by bubbling slowly through concentrated sodium hydroxide, followed by evaporation under reduced pressure.

The product was analyzed for amine content (Total, secondary plus tertiary and tertiary) via potentiometric titration, (see Official and Tentative Methods of the American Oil Chemists Society; Tf 1a-64 and Tf 2a-64).

Results of Titration—Example 2

Total amine (1°+2°+3°): $1000 \times 10^{-6}$ mol/g

Secondary plus tertiary amine (2°+3°): $1049 \times 10^{-6}$ mol/g

Tertiary amine (3°): $929 \times 10^{-6}$ mol/g

The results show that 93% of the total amine present was of the tertiary form.

EXAMPLE 3

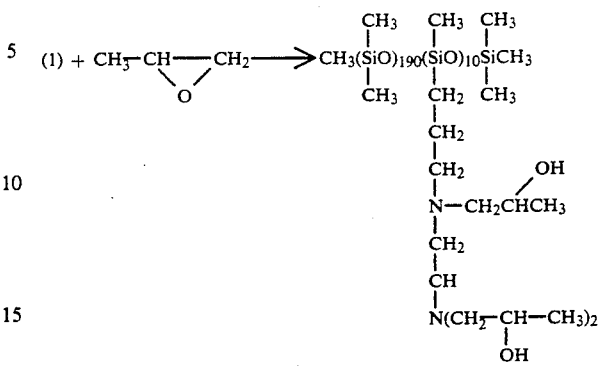

As in Example 2, 250 g of Amodimethicone Oil (1) and 33 g of propylene oxide were reacted initially at 50° C. and 100 psi until an exotherm of approximately 70° C. was observed. Following the exotherm, the reaction was done at 100° C. and 100 psi for about 20-24 hours. The product was "stripped" and analyzed as in Example 2.

Results of Titration—Example 3

Total amine: $1110 \times 10^{-6}$ mol/g
Secondary plus tertiary amine: $1077 \times 10^{-6}$ mol/g
Tertiary amine: $947 \times 10^{-6}$ mol/g
Approximately 85% of total amine was converted to tertiary form.

EXAMPLE 4

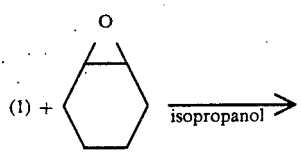

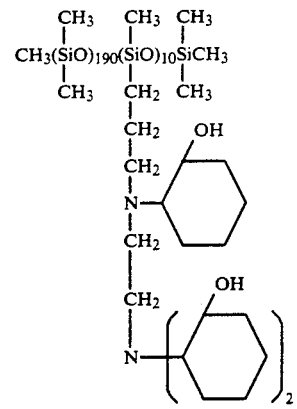

As in Example 2, 75 g of (1) and 13.9 g of cyclohexene oxide (Aldrich) together with 90 g of isopropanol (solvent-) were placed in the pressure reactor and reacted initially at 50° C. and 100 psi for about 1 hour during which time an exotherm to 63° C. was observed. The final conditions were set at 100° C. and 100 psi and the reaction allowed to run for 20-24 hours. The product was placed in a rotary evaporator and the solvent (isopropanol) removed under vacuum and heating. Analysis of product (brown was conducted as in Example 2.

Results of Titration—Example 4

Total amine: $1070 \times 10^{-6}$ mol/g
Secondary plus tertiary amine: $1075 \times 10^{-6}$ mol/g
Tertiary amine: $96 \times 10^{-6}$ mol/g About 9% of the total amine content was converted to the tertiary form.

EXAMPLE 5

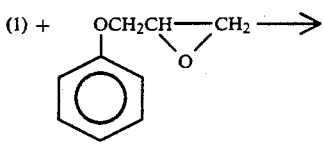

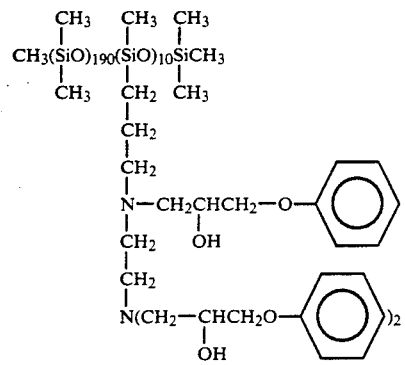

As in Example 4, 772 g of (1) and 22 g of 1,2 epoxy-3-phenoxy propane ex Aldrich) and 95 g of 2-propanol were reacted together for 24 hours. The product was light brown in appearance. The amine content was determined as in Example 2.

Titration Results—Example 5

Total amine: $530 \times 10^{-6}$ mol/g
Secondary plus tertiary amine: $526 \times 10^{-6}$ mol/g
Tertiary amine: $446 \times 10^{-6}$ mol/g

EXAMPLE 6

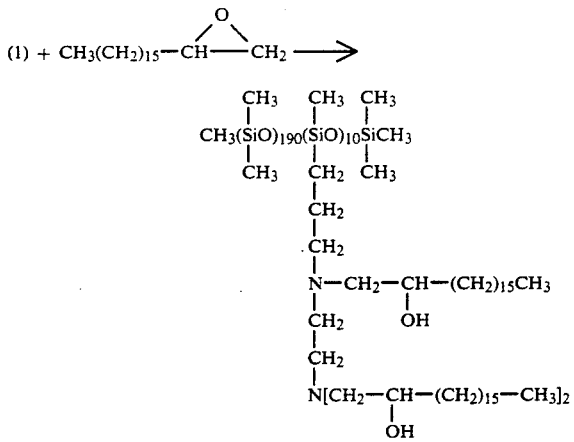

As in Example 4, 65 g of (1), 33 g of 1,2-epoxyoctadecane (ex Aldrich) and 100 g of isopropanol were reacted together. The final product was a solid yellowish 'wax' at room temperature which upon heating (45°-50° C.) becomes a viscous yellowish oil.

The product was analyzed as in Example 2 with one modification being made. It was necessary to use Toluene as a cosolvent together with acetic anhydride and glacial acetic acid since the product was found to be insoluble in a solution of acetic anhydride and glacial acetic acid alone.

Results of Titration—Example 6

Total amine: $754 \times 10^{-6}$ mol/g
Secondary plus tertiary amine: $673 \times 10^{-6}$ mol/g
Tertiary amine: $611 \times 10^{-6}$ mol/g About 81% of the total amine content was converted to the tertiary form.

Alkylation of Amino Functional Polydimethylsiloxane Copolymer

EXAMPLE 7

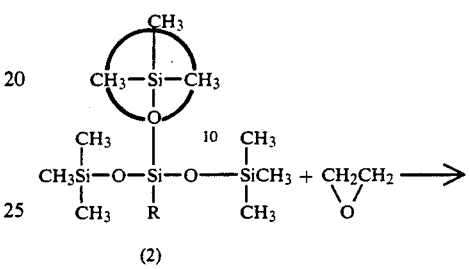

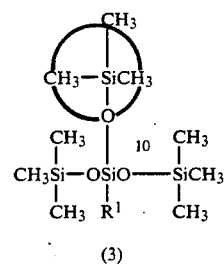

where R = $(-CH_2)_3-NH-(CH_2)_2-NH_2$ $R^1$ = $(-CH_2)_3-N-(CH_2)_2-N(CH_2CH_2OH)_2$
            |
            $CH_2CH_2OH$ As in Example 1, 100 g of silicone fluid (2), 11.6 g of ethylene oxide and 110 g of 2-propanol were reacted together. The reaction conditions were 50° C. and 100 psi for 24 hours. The final stripped product was milky white in appearance. There were two changes made in the analysis of the product. First, chloroform was the solvent chosen for total as well as secondary plus tertiary amine determination since the product was insoluble in a solution of ether and isopropanol. Second, the hydrochloric acid titrant was 0.2N. The same phenomenon, observed in Example 6 where the titrating solution became turbid and formed a precipitate, was observed when titrating this product for total and secondary plus tertiary amine content. The titration showed that all amines were converted to tertiary amines.

EXAMPLE 8

Anticaries property of aminosilicones as demonstrated by the dissolution test of hydroxyapatite powder.

In these sequential exposure experiments, hydroxy apatite powder (3.5%) was first treated with a 5% silicone emulsion (60-70 ml) for ten minutes, filtered, washed with distilled water, and then exposed in a pH 5, 150 ml acetic acid solution. Aliquots were withdrawn at various time intervals and filtered off the hydroxyapatite powder. The amounts of phosphate ion in the aliquots were measured by spectrophotometry at 710 nm with molybdate solution in accordance with Official Methods of Analysis, Association of Official Analytical Chemists, edited by Sidney Williams, Arlington, Virginia, p. 632 (1984). The results are shown in Table 1.

The ethoxylated aminoalkyl silicone had the structure of (4) in Example 2. The purpose of the experiment was to determine whether aminosilicones with tertiary amines are effective anticaries agent. The results are given in Table 1.

TABLE 1

ACID DISSOLUTION TESTS OF HYDROXYAPATITE POWDER WHICH WAS TREATED WITH AMINOSILICONES

| | 5 Min. | 10 Min. | 20 Min. | 30 Min. | 40 Min. | 50 Min. | 60 Min. |
|---|---|---|---|---|---|---|---|
| Sequential exposure | | | | | | | |
| Ethoxylated Aminoalkyl silicone | 316 | 350 | 370 | 381 | 357 | 386 | 366 |
| Polydimethylsiloxane | 344 | 358 | 380 | 404 | 380 | 431 | 417 |
| Untreated HAP | 373 | 432 | 425 | 447 | 444 | 440 | 438 |

This experiment demonstrates that after 60 minutes exposure to the acid solution, the untreated powder lost 438 ppm phosphate ions whereas the one treated with the modified aminoalkyl silicone of the invention lost only 366 ppm phosphate ion.

Toothpastes according to the invention were prepared by adding ingredients into a Hobart mixer and mixing until the mixtures became homogeneous pastes. Their ingredients are given in Examples 9–15 in w/w %.

EXAMPLE 9

| Natrosol 250M | 1.25% |
|---|---|
| Glycerine | 27% |
| Water | 10% |
| Alumina | 50% |
| $TiO_2$ | 0.5% |
| Chlorhexidine gluconate | 4.25% |
| Flavor 77171 | 1% |
| Propoxylated aminoalkylsilicone (Cpd (1) reacted with Propylene oxide-- see Example 3) | 4% |
| Lauramine oxide | 1% |
| Cocamine oxide | 1% |

Natrosol 250M is a hydroxyethylcellulose (a nonionic water-soluble polymer) gum available from Hercules, Inc., Wilmington, Del. Alumina 331 is $Al_2O_3$ trihydrate abrasive available from Aluchem. Flavor 77171 is available from International Flavors and Fragrances. Lauramine oxide and Cocamine oxide are surfactants from Armak Industrial Chemicals Division.

EXAMPLE 10

| Natrosol | 1.25% |
|---|---|
| Glycerine | 27% |
| Water | 10% |

-continued

| Alumina 331 | 50% |
|---|---|
| $TiO_2$ | 0.5% |
| Chlorhexidine gluconate | 4.25% |
| Flavor 77171 | 1% |
| Ethoxylated aminoalkylsilicone (Cpd (1) reacted with ethylene oxide-- see Example 2) | 4% |
| Lauramine oxide | 1% |
| Cocamine oxide | 1% |

EXAMPLE 11

| Glycerine | 7% |
|---|---|
| Water | 15% |
| Kelcoloid-S | 1% |
| Polyol III | 16% |
| Alumina 331 | 49% |
| Chlorhexidine gluconate | 4% |
| Flavor 77171 | 1% |
| Propoxylated aminoalkylsilicone (Cpd (1) reacted with propylene glycol) | 2% |
| Arocel - 80 | 1% |
| Tween - 80 | 1% |

Kelcoloid-S is a propylene glycol alginate gum available from Kelco of Clark, N.J. Polyol III is a mixture of sorbitol and hydrogenated corn syrup available form Roquette Corporation. Aracel-80 and Tween-80 are surfactants available from ICI Americas and are, respectively, sorbitan oleate and polysorbate-80.

EXAMPLE 12

| Glycerine | 7% |
|---|---|
| Water | 15% |
| Kelcoloid-S | 1% |
| Polyol III | 16% |
| Alumina 331 | 49% |
| Chlorhexidine gluconate | 4% |
| Flavor 77171 | 1% |
| Ethoxylated aminoalkylsilicone (Cpd (1) reacted with ethylene oxide-- See Ex. 2) | 1% |
| Aracel - 80 | 1% |
| Tween - 80 | 4% |

EXAMPLE 13

| Glycerine | 7% |
|---|---|
| Kelcoloid-S | 2% |
| Sorbitol | 14% |
| Alumina 331 | 42.6% |
| Chlorhexidine gluconate | 4% |
| Flavor 77171 | 1% |
| Propoxylated aminoalkylsilicone (Cpd (1) reacted with Propylene glycol) | 4% |
| Arocel - 80 | 1% |
| Targitol NP-15 | 0.5% |
| Water | 19.9 |

Pluronic F-87                4%

Pluronic F-87 is Polyoxy Propylene Polyoxyethylene Block Copolymer surfactant available from BASF-Wyandotte of Parsippany, N.J. Tergitol NP-15 is Polyoxyethylene (15) Nonyl Phenyl Ether surfactant available from Union Carbide.

EXAMPLE 14

| Glycerine | 7% |
|---|---|
| Water | 11.3% |
| Polyol III | 20.6% |
| Alumina 331 | 47.7% |
| TiO$_2$ | 0.5% |
| Hercules WSPM 1017 | 1.3% |
| Chlorhexidine gluconate | 4.1% |
| Flavor 77171 | 1% |
| Propoxylated aminoalkylsilicone (Cpd (1) reacted with propylene oxide) | 4.1% |
| Arlocel - 60 | 0.9% |
| Tween - 60 | 1.1% |

Hercules WSPM 1017 (experimental) is a lauryl cellulose ether gum. Arlacel-60 is a sorbitan stearate surfactant available from ICI Americas. Tween-60 is polysorbate-60, also available from ICI Americas.

EXAMPLE 15

| Glycerine | 7.2% |
|---|---|
| Water | 11.3% |
| Polyol III | 20.6% |
| Alumina 331 | 47.7% |
| TiO$_2$ | 0.5% |
| Hercules WSPM 1017 | 1.3% |
| Chlorhexidine-gluconate | 4.1% |
| Flavor 77171 | 1% |
| Ethoxylated aminoalkylsilicone (Cpd (1) reacted with ethylene oxide-- See Ex. 2) | 4.1% |
| Arlocel - 60 | 0.9% |
| Tween - 60 | 1.1% |

EXAMPLE 16

Aldehyde Chemical Reactivity Test of Aminosilicones

To assess the aldehyde chemical reactivity of aminosilicones, various aminosilicone emulsions were mixed with 2-furaldehyde and stored in the dark overnight to develop colors. The 2-furaldehyde was distilled before use. The following mixtures were prepared:

| Solution No. | Ingredients |
|---|---|
| 1 | chlorhexidine + furaldehyde + glycine |
| 2 | furaldehyde + an aminoalkylsilicone |
| 3 | furaldehyde + ethoxylated aminoalkyl silicone |
| 4 | furaldehyde + propoxylated aminoalkyl silicone |
| 5 | furaldehyde + DC-929 |
| 6 | furaldehyde + PS343 |
| 7 | chlorhexidine + aminoalkylsilicone |
| 8 | chlorhexidine + ethoxylated amino alkylsilicone |
| 9 | chlorhexidine + furaldehyde |
| 10 | furaldehyde |
| 11 | chlorhexidine + propoxylated amino alkylsilicone |

The aminoalkylsilicone which was used was compound (1) of Example 2. The ethoxylated compound was an ethoxylated Cpd (1) (See Example 2). The propoxylated compound was a propoxylated Cpd (1) (See Example 3). The amino alkyl silicone and modified aminoalkyl silicones were used in nonionic emulsions of 30% solid.

DC-929 is a cationic emulsion from Dow Corning. PS343 is a nonionic emulsion of 15% polydimethylsiloxane (M.W. 26,000).

These solutions were then ranked by their color intensity.

| 2> | 1> | 5>> | 3,9,4> | 6,10> | 8,11> | 7 |
|---|---|---|---|---|---|---|
| very dark brown | brown | brown orange | yellow | very light yellow | cloudy white | cloudy colorless |

The primary amine-containing amodimethicones (#2 and #5) all developed intensive colors whereas the tertiary amine-containing ones (#3 and #4) developed yellow colors; their intensities were close to the control solution (#10). The PS343, which did not have amine functional groups, developed colors equivalent to the control.

These results demonstrated that the aminosilicones of the invention have an inherently reduced chemical reactivity with the potential staining aldehyde chemical agents.

EXAMPLE 17

Mouthwash

A prophetic formula for a mouthwash is as follows:

| INGREDIENT | CONC. % |
|---|---|
| Modified Amodimethicone prepared in Ex. 2 | 1.00 |
| Lauramine Oxide ex. Armak Aromox DMMC-W | 0.30 |
| Water | 45.84915 |
| 96% Glycerin USP | 50.00 |
| Ethanol | 2.00 |
| Flavor | 0.25 |
| D&C Yellow #10 | 0.00060 |
| FD&C Blue #1 | 0.00025 |
| 20% Chlorhexidine Digluconate ex. Lonza Spectrodyne G. | 0.60 |

The mouthwash is made by dissolving 0.2% lauramine oxide in water. The amodimethicone is then added and emulsified. The emulsion thus prepared is added to glycerin and mixed. 0.1% lauramine oxide in ethanol is then dissolved in the mixture, flavor is added to ethanol and mixed, then added to the above mixture. The colors are added and mixed. Finally, chlorhexidine is added and mixed. A mouthwash results.

EXAMPLE 18

A prophetic formula for a clear mouthwash is as follows:

| INGREDIENT | CONC. % |
| --- | --- |
| 70% Sorbitol Soln. | 50.00 |
| Water | 43.69915 |
| Modified Amodimethicone prepared in Ex. 3 | 1.00 |
| Tergitol NP15 | 0.39 |
| Water | 2.06 |
| Ethanol (200PF) | 2.00 |
| Flavor | 0.25 |
| D&C Yellow #10 | 0.00060 |
| FD&C Blue #1 | 0.00025 |
| 20% Chlorhexidine Digluconate ex. Lonza Spectrodyne G. | 0.60 |

The mouthwash is prepared as follows:

Sorbitol and water are mixed. The amodimethicone is emulsified with 0.09% tergitol and water and added to the sorbitol/water mixture. 0.30% tergitol is dissolved in ethanol and flavor is added. After mixing, the flavor mixture is added to the silicone emulsion. Colors are added and mixed. Finally, chlorhexidine is added and the preparation is mixed. A clear mouthwash is obtained.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

We claim:

1. A dentifrice comprising from 0.5 to 100 wt. % of an aminoalkylsilicone having a molecular weight above 5000 including at least one unit of formula A:

$$R^2_m NH_{2-m}(CH_2CH_2NH_{1-b}) - R^1 - SiO_{(3-a)/2} \quad A$$
$$\underset{R^2_b}{|} \quad \underset{R_a}{|}$$

wherein
a is from 0 to 2, n is from 1 to 5, R is a monovalent radical, $R^1$ is a divalent hydrocarbon radical, $R^2$ is $$-CH_2CHR^3,$$
$$\underset{OH}{|}$$

$R^3$ is selected from the group consisting of hydrogen and monovalent hydrocarbon radicals, b is 0 or 1, and m is 1 or 2 in an orally acceptable vehicle.

2. The dentifrice of claim 1 wherein said unit is $$(HOCH_2CH_2)_2NCH_2CH_2N-CH_2CH_2CH_2SiO-$$
$$\underset{CH_2}{|} \quad \underset{CH_3}{|}$$
$$\underset{CH_2}{|}$$
$$\underset{OH}{|}$$

3. The dentifrice of claim 1 wherein n is 1.

4. The dentifrice of claim 1 wherein R is selected from the group consisting of hydrocarbon radicals, halogenated hydrocarbon radicals, hydrogen, hydroxyl and alkoxyl.

5. The dentifrice of claim 1 wherein R is selected from the group consisting of methyl, phenyl and -trifluoropropyl.

6. The dentifrice of claim 1 wherein $R^1$ comprises 3 or more carbon atoms.

7. The dentifrice of claim 1 wherein $R^3$ is selected from the group consisting of hydrogen, methyl and phenyl 8. The dentifrice of claim 1 further comprising at least one unit of formula B, $$R_a^5 R_c^4 SiO_{(4-a-c)/2} \quad B$$

wherein $R^4$ and $R^5$ are the same or different monovalent radicals, a and c are integers of 0, 1, 2 or 3 and a plus c is 0, 1, 2 or 3.

9. The dentifrice of claim 8 wherein $R^4$ and $R^5$ are independently selected from the group consisting of hydrocarbon radicals, halogenated hydrocarbons, hydrogen and alkoxyls.

10. The dentifrice of claim 9 wherein $R^4$ and $R^5$ are independently selected from the group consisting of methyl, phenyl and -trifluoropropyl.

11. The dentifrice of claim 8 wherein a plus c equals 2.

12. The dentifrice of claim 8 comprising a toothpaste including a humectant and an abrasive.

13. The dentifrice of claim 8 comprising a mouthwash which includes ethanol.

14. The dentifrice of claim 8 wherein unit A comprises from 5 to 30% by repeat unit.

15. The dentifrice of claim 8 wherein units of formula A comprise from 1 to 10% by weight.

16. The dentifrice of claim 8 having a molecular weight of between 5,000 and 100,000.

17. The dentifrice of claim 8 having the formula $$Me_3SiO(Me_2SiO)_x(MeSiO)_ySiMe_3$$
$$\underset{CH_2}{|}$$
$$\underset{CH_2}{|}$$
$$\underset{CH_2}{|}$$
$$\underset{N-CH_2CH_2OH}{|}$$
$$\underset{CH_2}{|}$$
$$\underset{CH_2}{|}$$
$$\underset{N-CH_2CH_2OH}{|}$$
$$\underset{CH_2CH_2OH}{|}$$

wherein x and y are randomly arranged and x is from 750 to 1250 and y is from 25 to 100.

18. The dentifrice of claim 8 having the formula

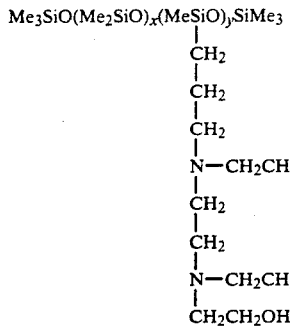

wherein the aminoalkylsilicone is a block copolymer and x is from 750 to 1250 and y is from 25 to 100.

19. The dentifrice of claim 1 further comprising chlorhexidine.

20. The dentifrice of claim 3 further comprising chlorhexidine.

21. The dentifrice of claim 5 further comprising chlorhexidine.

22. The dentifrice of claim 8 further comprising chlorhexidine.

23. A dentifrice comprising an aminoalkylsilicone copolymer including:

a) at least one unit of

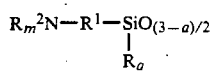   C wherein
a=0-2, m =1-2
R is a monovalent radical,
$R^1$ is a divalent hydrocarbon radical,
$R^2$ is

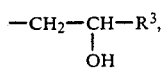

$R^3$ is a monovalent hydrocarbon radical or hydrogen, and b) at least one unit of $R^5{}_aR^4{}_cSiO_{(4-a-c)/2}$ wherein $R^5$ and $R^4$ are the same or different monovalent radicals, a and c are integers of 0, 1, 2 or 3 and a plus c is 1, 2 or 3 in an orally acceptable vehicle.

24. The dentifrice of claim 23 wherein R is selected from the group consisting of hydrocarbon radicals, halogenated hydrocarbon radicals, hydrogen, hydroxyl and alkenyls.

25. The dentifrice of claim 23 wherein R is selected from the group consisting of methyl, phenyl and -trifluoropropyl.

26. The dentifrice of claim 23 wherein $R^1$ comprises a divalent hydrocarbon radical having 3 or more carbons.

27. The dentifrice of claim 23 wherein $R^3$ is selected from the group consisting of hydrogen, methyl or phenyl.

28. The dentifrice of claim 23 wherein $R^4$ and $R^5$ are independently selected from the group consisting of hydrocarbon radicals, halogenated hydrocarbons, hydrogen, hydroxyl and alkoxyls.

29. The dentifrice of claim 23 wherein $R^4$ and $R^5$ are independently selected from the group consisting of methyl, phenyl and -trifluoropropyl.

30. The dentifrice of claim 23 wherein a plus c is equal to 2.

31. The dentifrice of claim 23 comprising a toothpaste including abrasive and humectant.

32. The dentifrice of claim 23 comprising a mouthwash including ethanol.

33. The dentifrice of claim 23 wherein the aminoalkylsilicone has a molecular weight of between 5,000 and 100,000.

34. The dentifrice of claim 23 further comprising chlorhexidine.

35. The dentifrice of claim 23 wherein the % by repeat unit of Formula C is between 5 and 30%.

36. The dentifrice of claim 23 wherein the % by weight of aminosilicone units of formula C is between 1 and 10%.

37. The dentifrice of claim 34 wherein the concentration of chlorhexidine is from 0.001% to about 4% by weight.

38. The dentifrice of claim 1 wherein $R^1$ comprises 20 or fewer carbon atoms.

39. The dentifrice of claim 1 wherein $R^1$ comprises 3 carbon atoms.

40. The dentifrice of claim 23 wherein $R^1$ comprises 3 carbon atoms.

41. The dentifrice of claim 23 wherein $R^1$ comprises 20 or fewer carbon atoms.

* * * * *